United States Patent [19]
Goodell et al.

[11] Patent Number: 5,092,184
[45] Date of Patent: Mar. 3, 1992

[54] CELL STAINING SYSTEM FOR FLOW CYTOMETRY

[75] Inventors: Estelle M. Goodell, Otsego; Roger H. Davidson, Jr., Hartwick, both of N.Y.

[73] Assignee: Medical Research Institute of The Mary Imogene Bassett Hospital, Cooperstown, N.Y.

[21] Appl. No.: 455,592

[22] Filed: Dec. 22, 1989

[51] Int. Cl.⁵ .............................................. G01N 1/00
[52] U.S. Cl. ............................................... 73/863.32
[58] Field of Search ........... 73/863.32, 864.17, 864.24, 73/864.25; 422/100

[56] References Cited

U.S. PATENT DOCUMENTS

| | | |
|---|---|---|
| D. 248,045 | 5/1978 | Bassett et al. |
| D. 250,348 | 11/1978 | Frangiosa et al. |
| 3,807,235 | 4/1974 | Lefkovits et al. |
| 3,938,958 | 2/1976 | Lanier et al. ................ 73/863.32 |
| 3,982,438 | 9/1976 | Byrd |
| 4,158,035 | 6/1979 | Haase et al. |
| 4,459,864 | 7/1984 | Cirincione ........................ 422/100 |
| 4,478,094 | 10/1984 | Salomaa et al. .............. 73/863.32 |
| 4,599,315 | 7/1986 | Terasaki et al. |
| 4,621,667 | 11/1986 | Eberle ............................. 422/100 |
| 4,925,629 | 5/1990 | Schramm ........................ 422/100 |

OTHER PUBLICATIONS

Braylan et al., "Immunophenotyping of Leukemias and Lymphomas in Microtiter Trays," *Cytometry Supplement*, (1988) vol. 2, p. 52.

Edwards et al., "Efficient Use of Monoclonal Antibodies for Immunofluorescence," *Cytometry*, (1989) vol. 10, pp. 94–97.

Gitter et al., "Cytofluorometric Isolation of 1937," *J. of Immunology*, (1985) vol. 134, pp. 280–283.

Ledbetter et al., "T Cell Subsets Defined By Expression of Lyt-1,2,3 and Thy-1 Antigens," *J. Exp. Med.*, (1982) vol. 152, pp. 280–295.

Lindqvist et al., *Immunology*, (1987) vol. 60, pp. 579≧584.

*Primary Examiner*—Robert Raevis
*Attorney, Agent, or Firm*—Maurice M. Klee

[57] ABSTRACT

A pipetting system is provided which includes 1) a microtiter plate, 2) a multichannel pipette, and 3) a rack for recieving the microtiter plate and the multichannel pipette. The rack includes multiple rows corresponding to the rows of the microtiter plate. The rack and the multichannel pipette are constructed so that for each row, the pipette can be inserted in the rack in only one left/right orientation. In this way, errors due to misorientations of the pipette with the wells of the microtiter plate are eliminated. Methods for staining cells for flow cytometry using the pipetting system are also disclosed.

18 Claims, 3 Drawing Sheets

CELL STAINING SYSTEM FOR FLOW CYTOMETRY

BACKGROUND OF THE INVENTION

1. Field of the Invention

This invention relates to flow cytometry and, in particular, to a method and apparatus for staining cells for subsequent analysis and/or sorting in a flow cytometer.

2. Description of the Prior Art

Flow cytometers are widely used to sort and quantify specific cell types within a population of cells. One common application of the procedure involves the quantification of lymphocyte subsets within a leukocyte population. Such quantification is of importance in various diseases, including AIDS where one of the primary tests for evaluating patients involves measuring the level of CD4+ lymphocytes in peripheral blood samples.

A flow cytometric analysis involves two basic steps: 1) staining selected cell types, and 2) determining the number of stained cells relative to the total number of cells in the population. The present invention is concerned with the staining step. Commercially available equipment, e.g., equipment manufactured by such companies as Coulter Electronics, Hialeah, Fla., and Becton-Dickinson, Mountain View, Calif., is widely available for performing the cell sorting and counting step of the analysis.

As presently practiced, staining of cells for flow cytometry is performed using antibodies, e.g., monoclonal antibodies, which recognize specific cell types within the population of cells. The antibodies are either directly labeled with a fluorescent compound or indirectly labeled using, for example, a fluorescent-labeled second antibody which recognizes the first antibody. Typically, a panel of antibodies is used to analyze the cell population, with samples of the population being stained with each of the antibodies in the panel and then analyzed in the flow cytometer.

The staining of a cell population with panel of antibodies involves multiple manipulative steps. First, a series of samples from the population are prepared. Then, one antibody from the panel is combined with each of the samples, and the resulting mixture is incubated so that the antibody can bind to the cells in the sample (if any) which the antibody recognizes. One or more washings of the cells are then performed to remove unbound antibody. If the first antibody has not been directly labeled with a fluorescent compound, additional incubations with other antibodies or reagents and additional washings are in general required to label the unconjugated primary antibody bound to the cells. Finally, the stained cells are transferred to the flow cytometer for sorting and analysis.

Plainly, a procedure having these many steps is difficult to perform efficiently and accurately. Moreover, because of the high level of concentration and attention to detail that is needed to avoid mistakes, the procedure as presently practiced does not lend itself to performance by relatively unskilled technicians, as is desired when large numbers of analyses are to be performed, e.g., in a clinical setting. An error in performing an analysis, if recognized, leads to a repeated procedure with a concomitant loss of time and reagents. An unrecognized error results in invalid data which can have devastating consequences, especially where patient management is involved.

At present, there is no uniform system for staining cells for flow cytometry. Each laboratory which adopts the technique is faced with the problem o developing its own protocols for conducting the various steps in the procedure. Although extensive efforts to develop suitable protocols have been made by researchers and supervisory personnel, there still does not exist a truly efficient and easy-to-perform technique for staining cells for flow cytometry.

Examples of the techniques which have been developed can be in found in the following references:

1. Braylan, R. C., Chen, M. G., Iturraspe, J. A., and Benson, N. A., "Immunophenotyping of Leukemias and Lymphomas in Microtiter Trays," *Cytometry Supplement*, (1988) vol. 2, page 52.
2. Edwards, B. S., and Shopp, G. M., "Efficient Use of Monoclonal Antibodies for Immunofluorescence," Cytometry, (1989) vol. 10, pages 94–97.
3. Gitter, B. D., Finn, O. J., and Metzgar, R. S., "Cytofluorometric Isolation of 1937, an Ia Antigen-Bearing Variant of the Ia-Negative Human Monocytic Cell Line U937," *J. of Immunology*, (1985) vol. 134, pages 280–283.
4. Ledbetter, J. A., Rouse, R. ".V, Micklem, H. S., and Herzenberg, L. A., T Cell Subsets Defined By Expression of Lyt-1,2,3 and Thy-1 Antigens," *J. Exp. Med.*, (1982) vol. 152, pages 280–295.
5. Lindqvist, C., Patarroyo, M., Beatty, P. G. and Wigzell, H., "A Monoclonal Antibody Inhibiting Leucocyte Adhesion Blocks Induction of IL-2 Production but not IL-2 Receptor Expression," *Immunology*, (1987) vol. 60, pages 579–584.
6. Loken, M. R. and Stall, A. M., "Flow Cytometry as an Analytical and Preparative Tool in Immunology," *J. Immunol. Methods*, (1982) vol. 50, pages R85–R112.
7. Muirhead, K. A., Wallace, P. K., Schmitt, T. C., Frescatore R. L., Franco, J. A., and Horan, P. K. "Methodological Considerations for Implementation of Lymphocyte Subset Analysis in a Clinical Reference Laboratory," *Annals New York Academy of Sciences*, (1986) vol. 468, pages 113–127.
8. Rector, E., Nakajima, T., Rocha, C., Duncan, D., Lestourgeon, D., Mitchell, R. S., Fischer", J., Sehon, A. H., and Delespesse, G., Detection and Characterization of Monoclonal Antibodies Specific to IgE Receptors on Human Lymphocytes by Flow Cytometry," *Immunology*, (1985) vol. 55, pages 481–488.

In particular, Loken et al. describe a staining procedure in which cells are aliquoted into a microtiter plate, pelleted, and the supernatants removed by suction. Thereafter, stains are added to the wells and the cells in each row are resuspended using an 8-channel multiple micropipette. After various incubation/washing steps, the cells are transferred to test tubes using a 4-channel multipipette for analysis in a flow cytometer.

The use of microtiter plates to perform staining is also described in Muirhead et al., Lindquist et al., Ledbetter et al., Edwards et al. and Gitter et al. The Edwards and Gitter references also describe centrifuging a microtiter plate and removing the supernatant liquid from the cell pellet by a single downward jerking motion or flicking of the plate. Braylan et al. describe an automated immunofluorescence flow cytometry technique using microtiter plates. Rector et al. describe a method for detecting antibodies in hybridoma supernatants using a flow cytometer technique in which 96-well V-bottomed microtiter plates, 96-well flat-bottomed microtiter plates, and microcentrifuge tubes were used to conduct the various reactions and in which transfer between the V-bottomed and flat-bottomed microtiter plates was performed using a multichannel pipette.

The use of multichannel pipettes with microtiter plates is also shown in U.S. Pat. Nos. 3,807,235, 3,982,438, and 4,158,035. In each of these patents, the multichannel pipette is mounted on a supporting member and either the pipette is moved vertically relative to the plate or the plate is moved vertically relative to the pipette when pipetting is to performed.

In addition to the foregoing, U.S. Design Patents Nos. Des. 248,045 and Des. 250,348 show a pipette holder and a test tube rack, respectively, and U.S. Pat. No. 4,599,315 shows a microdroplet test plate and a cover for the plate, where the cover and the plate have a corresponding set of letters and numbers. Also, test tube strips and carriers for test tube strips of the type shown in FIG. 2 but without shoulders 62 and 64 are commercially available but have not been reported in the literature for use in the staining of cells for flow cytometry (see elements 74 and 82 in FIG. 2). From another commercial supplier, individual tubes have been described for holding small cell samples that are received in the glass sample chamber of an Epics C Flow Cytometer manufactured by Coulter Electronics. Such tubes, however, have not been supplied as a test tube strip in a carrier that would be conformationally compatible with a multichannel pipette and microtiter plate.

SUMMARY OF THE INVENTION

In view of the foregoing state of the art, it is an object of the present invention to provide an improved method for staining cells for flow cytometry. More particularly, it is an object of the invention to provide an overall system which promotes the efficient and accurate handling of the reagents used in immunofluorescent labeling of cell surface molecules for analysis by flow cytometry.

It is a further object of the invention to provide specialized apparatus for practicing the improved staining method so as to make the method efficient, accurate, and easy to perform in large quantities by relatively unskilled personnel.

It is also an object of the invention to provide a standardized staining system which has the necessary flexibility for both research and clinical use, is reliable and reproducible, and which reduces costs by minimizing time expenditure and reagent waste.

To achieve the foregoing and other objects, the invention in accordance with certain of its aspects provides a pipetting system which includes 1) an array of receptacles for holding one or more fluids, e.g., a microtiter plate or a test tube strip carried in a supporting frame, 2) a multichannel pipette, and 3) a rack for receiving the array of receptacles and the multichannel pipette.

The rack and the multichannel pipette are constructed so that the pipette can be inserted in the rack in only one orientation (hereinafter referred to as a "single-orientation rack" and a "singleorientation pipette", respectively). In this way, pipetting errors due to inadvertent left-side/rightside inversions of the multichannel pipette, i.e., 180° rotations of the multichannel pipette, are avoided. Similarly, in certain preferred embodiments, the array of receptacles and the portion of the rack which receives the array are constructed so that the array can only be inserted in the rack in one orientation (hereinafter referred to as a "single-orientation receptacle array"). Again, this eliminates pipetting errors resulting from misorientations between the multichannel pipette and the array of receptacles.

In connection with other preferred embodiments, the array of receptacles has a series of rows, e.g., the array is in the form of an 8×12 microtiter plate, and the single-orientation pipette can be received in the single-orientation rack in a number of positions, each position corresponding to one row of the receptacle array. As with the single row embodiment, for each of the positions, the multichannel pipette can only be received in the rack in one orientation, the orientation being the same for all of the positions. Again, this prevents errors due to inadvertent rotation of the multichannel pipette.

For the multi-row embodiment, the rack preferably includes a system for indicating when the multichannel pipette has been used with a particular row. In this way, mistakes due to row skipping or erroneous multiple operations on a single row are avoided. In addition to indicating when a row has been used, the rack can also physically inhibit multiple uses of the multichannel pipette with individual rows.

By means of the foregoing apparatus, the invention also provides improved methods for staining cells and for transferring stained cells to a flow cytometer. In particular, cells can be efficiently and accurately stained with a panel of stains by 1) placing the stains into a first array of receptacles, e.g., the test tubes of a test tube strip, 2) placing the cells to be stained into a second array of receptacles, e.g., the wells of a microtiter plate, using, for example, a single-orientation pipette and a single-orientation rack, and 3) transferring the stains from the first array of receptacles to the second array of receptacles using a single-orientation rack and a single-orientation pipette. In this way, the operator need not be concerned with mixing up the stains in the transfer process.

In addition to using a single-orientation rack to hold the second array of receptacles, a single-orientation rack can also be used to hold the first array of receptacles, e.g., in the case of a test tube strip by placing the strip in a carrier designed to mate with the rack. Also, if desired, the first array of receptacles and/or the second array of receptacles can be single-orientation receptacle arrays. In these ways, further assurance is provided that the correct stain ends up in the correct cell-containing receptacle.

By means of the multi-row embodiments, multiple cell populations and/or large panels of antibodies can be used. By use of the indicating system, the operator immediately knows which rows have been operated on, e.g., which rows stain has been removed from, which rows stain has been added to, and which rows cells have been added to. For further assurance against errors, the inhibiting system can be used in place of or in addition to the indicating system.

The apparatus of the invention also serves to improve the process of transferring stained cells to a flow cytometer. In this case, a single-orientation rack and a single-orientation pipette are used to transfer stained cells from, for example, a microtiter plate to an array of receptacles compatible with the sample port of a flow cytometer. For example, the stained cells can be transferred to a test tube strip and the individual test tubes can be removed from the strip and placed in the flow cytometer's sample port. Alternatively, if the cytometer's sample port is designed to receive a larger vessel than an individual test tube from a test tube strip, the individual test tubes, if properly sized, can be placed in the larger vessel and that combination inserted in the cytometer's sample port. In accordance with these aspects of the invention, the single-orientation rack can be used with just the microtiter plate or can be used with both the microtiter plate and the array of receptacles compatible with the cytometer's sample port.

In sum, the apparatus of the invention serves to improve the accuracy, efficiency, and ease of performance of the entire procedure, beginning with the combining of the stains with the cells, and ending with the transferring of the stained cells to the cytometer.

BRIEF DESCRIPTION OF THE DRAWINGS

The accompanying drawings, which are incorporated in and constitute part of the specification, illustrate the preferred embodiments of the invention, and together with the description, serve to explain the principles of the invention. The aspects of the invention shown in each of the drawings are as follows.

DESCRIPTION OF THE PREFERRED EMBODIMENTS

Figure 1:
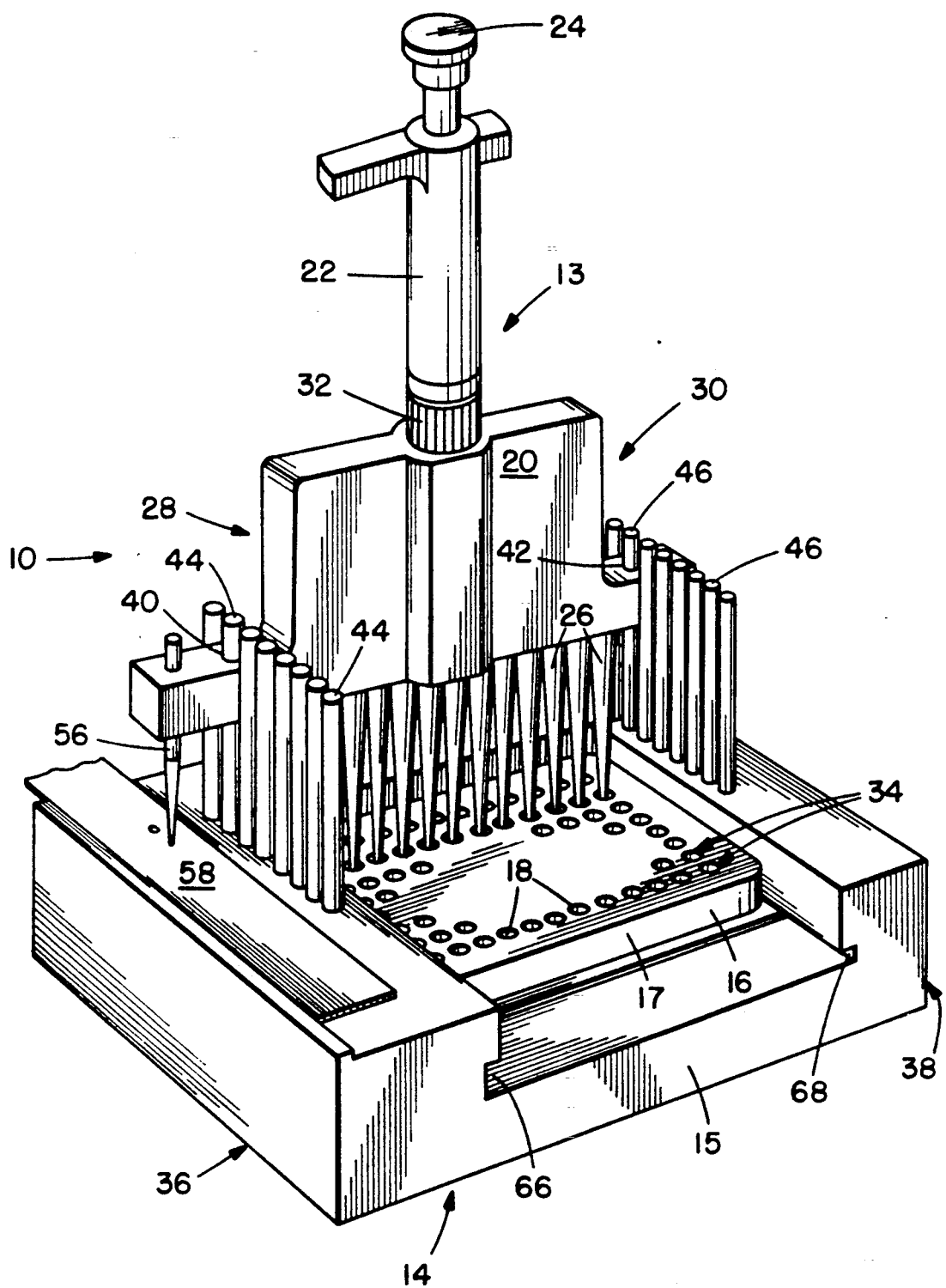
FIG. 1 is a perspective view of the pipetting system of the invention showing a single-orientation multichannel pipette, a single-orientation microtiter plate, and a single-orientation rack.

With reference now to the drawings, wherein like reference characters designate like or corresponding parts throughout the several views, there is shown in FIG. 1 a pipetting system 10 constructed in accordance with invention. As shown in this figure, pipetting system 10 includes single-orientation multichannel pipette 13, single-orientation rack 14, and single-orientation receptacle array 16 which in this figure is in the form of a microtiter plate having a body 17 and a plurality of wells (receptacles) 18 formed in the body and arranged in a series of rows 34.

As is conventional, multichannel pipette 13 includes body 20, handle 22, spring-loaded plunger 24, and an array of replaceable pipettes 26. The desired volume of fluid to be transferred is set by rotating the plunger 24. Pipette 13 is operated by depressing plunger 24 into handle 22. This causes fluids to be either drawn into or ejected from pipettes 26. For other pipette constructions known in the art, a control ring 32 is rotated to set the volume of fluid to be transferred. As seen from the front, pipette 13 and its body 20 have a left-hand side (first end) 28 and a right-hand side (second end) 30.

Similarly, rack 14 and its body 15 have a left-hand side (first end) 36 and a right-hand side (second end) 38. To prevent the multi-channel pipette 13 from being received in rack, 14 in the wrong orientation, pipette 13 includes orientation means 40,42 and rack 14 includes orientation means 44,46 which together insure that the pipette can be inserted in the rack only when the pipette's left and right hand sides 28,30 are associated with the rack's left and right hand sides 36,38, respectively.

Figure 3:
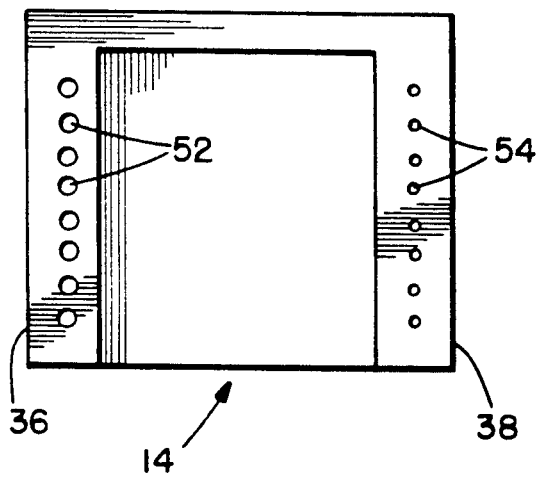
FIGS. 3 and 4 are top views of a single-orientation rack showing two alternative embodiments for achieving a single left/right orientation between a rack and a multichannel pipette.
Figure 4:
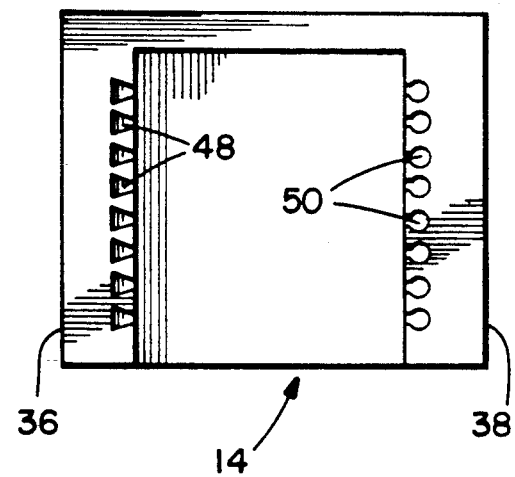

As shown in FIG. 1, orientation means 40,42 comprises apertures of different diameters, and orientation means 44,46 comprises pegs of different diameters corresponding to the diameters of the apertures. Although smaller peg 46 will fit into either aperture, larger peg 44 will only fit into aperture 40, thus preventing pipette 13 from being inserted in rack 14 with the pipette's right-hand side 30 associated with the left-hand side 36 of the rack. As also shown in FIG. 1, rack 14 includes an array of pegs 44,46 so that pipette 13 can be received in rack 14 in alignment with any of the rows 34 of microtiter plate 16, Other geometrical shapes besides circles of different diameters can be used to insure that pipette 13 can be received in rack 14 in only one orientation. For example, FIG. 4 illustrates the use of dovetail apertures 48 at the left-hand side 36 of rack 14 and circular apertures 50 at the right-hand side 38. For this embodiment, pipette 13 would have corresponding complementary structures (not shown) on its left and right hand sides, respectively. Similarly, FIG. 3 illustrates another manner in which circles of different diameters can be used to achieve single-orientation engagement of the pipette with the rack. In this case, apertures 52,54 of different sizes are formed in rack 14 and pipette 13 would have corresponding pegs of different sizes (not shown) to mate the apertures. Depending upon the design of the pipette and the rack, the use of apertures on the rack and pegs on the pipette may permit easier mating of the pipette with the rack than having pegs on the rack and apertures on the pipette as shown in FIG. 1.

Orientation means other than geometric shapes can also be used in the practice of the invention. For example, electrical, electromagnetic or electro-optical devices can be used to insure single orientation engagement. Thus, for example, pipette 13 can have a magna associated with one of its ends and rack 14 can allow engagement of the pipette with the rack only when the magnet is associated with, for example, the left-hand side of the rack. Other orientation mechanisms will be evident to persons skilled in the art from the disclosure herein.

Figure 2:
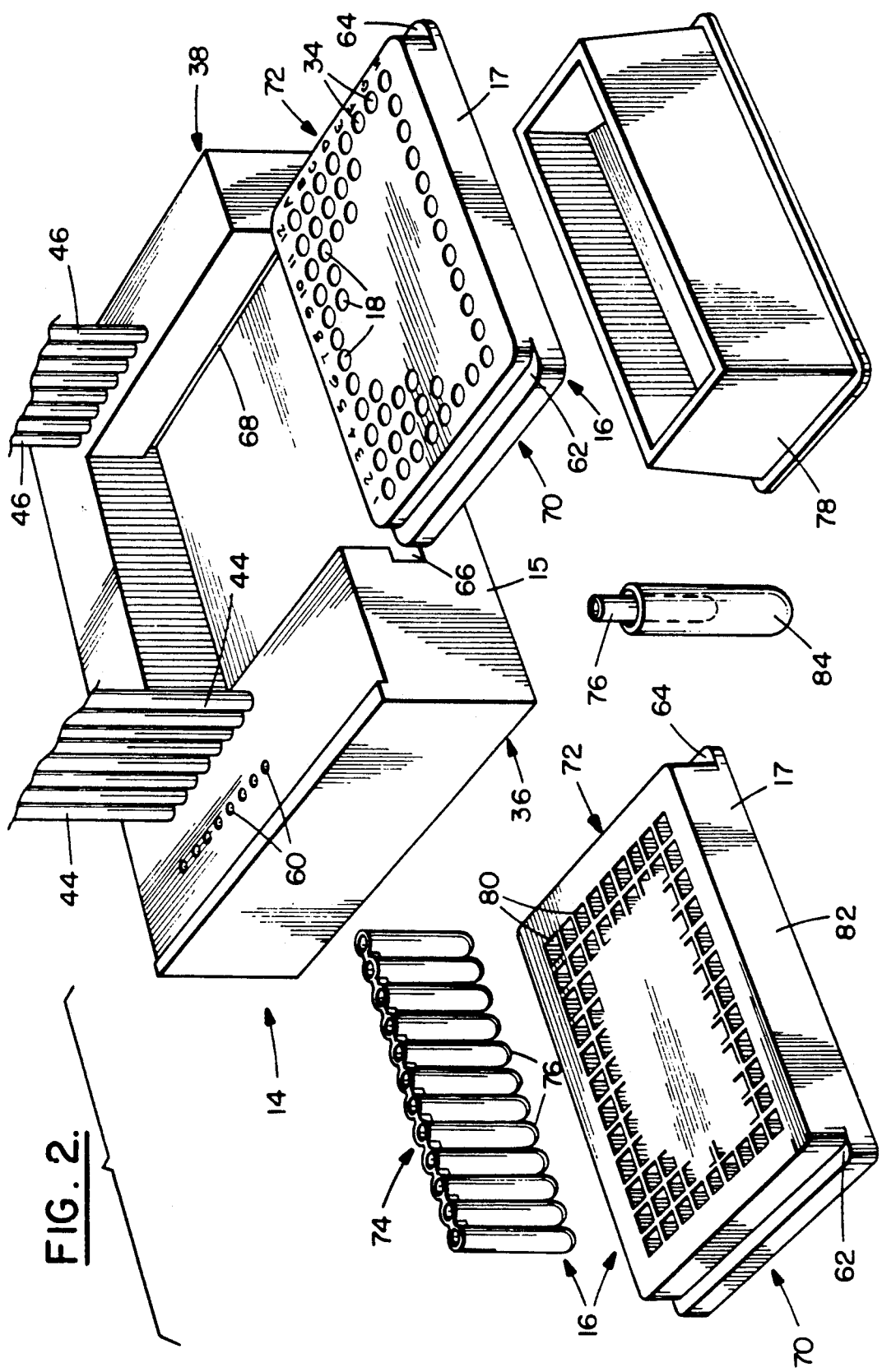
FIG. 2 is a perspective view illustrating in schematic form the us of the pipetting system of the invention in the staining of cells for analysis by flow cytometry.

As shown in FIG. 1, pipette 13 and rack 14 can include indicating means 56,58 for indicating when the pipette has been engaged with the rack in alignment with a particular row 34 of microtiter plate 16. As shown in this figure, the indicating means comprises a stylus which engages a strip of paper 58 carried by the rack. As shown in FIG. 2, rack 14 can include apertures 60 to facilitate the penetration of the stylus through the paper. Other indicating means, including electrical, electromagnetic, or electrooptical devices, can be used to record the engagement of the pipette with a particular row of the receptacle array is desired.

In addition to indicating means, rack 14 can also include means for inhibiting multiple engagements of pipette 13 with a particular row. For the embodiment of FIG. 1, this is accomplished by making either or both of pegs 44 and 46 removeable. In this way, once a row has been operated on, one or both of the pegs for that row can be removed, thus inhibiting further operations on that row. To reset the rack, pegs 44,46 are simply reinserted into the rack. Again, the inhibiting/resetting functions can be performed in other ways, e.g., electrically, if desired.

In addition to using orientation means for the engagement of pipette 13 with rack 14, orientation means can also be used to control the engagement of receptacle array 16 with rack 14. FIGS. 1 and 2 illustrate one such orientation means wherein the receptacle array 16 has shoulders 62 and 64 of different heights which mate with corresponding channels 66 and 68 of rack 14 which are also of different heights. In this way, the array 16 can only be mated with rack 14 when the left-hand side (first end) 70 of the array is associated with the left-hand side 36 of the rack and the right-hand side (second end) 72 of the array as associated with the right-hand side 38 of the rack as with orientation means used to control the engagement of the multichannel pipette with the rack, other means besides those illustrated can be used as the orientation means for the rack/receptaclearray combination.

With reference now to the method aspects of the invention, FIG. 2 illustrates typical apparatus for use in staining cells for flow cytometry in accordance with the invention. The apparatus includes a rack 14 and a microtiter plate 16 having the characteristics described above. The apparatus also includes test tube strip 74 composed of individual test tubes 76. Test tube strip 74 is received in apertures 80 of body 17 of carrier or frame 82, and the combination of the tube strip with the carrier forms an array of receptacles which can be received in rack 14. The apparatus of FIG. 2 also includes a reservoir 78 for holding, for example, the cells to be stained, and a vessel 84 compatible with the sample port of a flow cytometer for holding individual test tubes 76 from test tube strip 74.

A typical application of the apparatus of FIG. 2 to the staining of cells for flow cytometry is as follows. A panel of antibodies at the working concentrations for the antibodies are placed into individual test tubes 76 of one or more test tube strips 74. The test tube strips are placed into a carrier 82 (preferably, but not necessarily, a single-orientation carrier), and the carrier is engaged with a first single-orientation rack 14. A microtiter plate 16 having, for example, V-bottom wells, (preferably, but not necessarily, a single-orientation plate), is placed into a second single-orientation rack 14.

Using a single-orientation pipette 13 having a capacity of, for example, 5-50 microliters, a portion of the panel of antibodies, e.g., twenty microliters, is transferred from the test tubes of the test tube strips to the wells of the microtiter plate. As the transfer is made, stylus 56 and paper strip 58 on each of the two single-orientation racks provides a ready indication to the operator of which rows antibodies have been removed from, in the case of the test tube strips, and which rows antibodies have been added to, in the case of the microtiter plate.

Following this transfer (or alternatively prior to the antobody transfer), the cells to be stained are added to the wells using for example, reservoir 78 to hold the cells and a single-orientation pipette to make the transfer. The cells can be at a concentration of between, for example, $25 \times 10^6$ and $100 \times 10^6$ cells/milliliter, and ten microliters of the cell suspension can be added to each well. Again, stylus 56 and paper strip 58 provide an initiation of the rows to which cells have been added. (Note that in general a new paper strip 58 is placed on rack 14 at the beginning beginning of each transfer operation. Alternatively, a family of single-orientation pipettes which produce marks in different locations of produce marks of different types can be used so that at the end of the analysis, the paper strip contains a record of all of the transfers which have been performed.)

The cells and the antibodies are then incubated for a period of time sufficient for the antibodies to bind to the cells in the suspension (if any) which the antibodies recognize, e.g., for 30 minutes at 4° C. Thereafter, the cells are washed to remove unbound antibody. The washing can be done using, for example, phosphate buffered saline (PBS) supplemented with 1% bovine plasma albumin (BPA). By means of a reservoir 78 and a single-orientation pipette having a capacity of, for example, 50-200 microliters, a quantity of wash solution, e.g., 200 microliters, is transferred to each well. Again, stylus 56 and paper strip 58 provide a record of the addition of the wash solution to the various rows of the microtiter plate. The microtiter plate is then centrifuged, e.g., at 4° C. for 5 minutes at 200 × g, the supernatant is removed by, for example, flicking the plate, and, as appropriate, one or more additional washes are performed to insure removal of unbound antibody. The centrifuging of the microtiter plate can be performed with the plate removed from the single-orientation rack or, depending upon the design of the rack, with the plate and the rack combined as a unit.

For unlabeled primary antibodies, labeling is then performed by resuspending the cells in, for example, 25 microliters of fluorescent-labeled secondary antibody and incubating the antibody/cell mixture for a period of time sufficient for the labeled antibody to bind to the unlabeled antibodies, e.g., for 30 minutes at 4° C. Again, a single-orientation rack and a singleorientation pipette can be used for this transfer. After the incubation, the cells are again washed with, for example, PBS, using the procedures described above.

The cells are now ready for sorting and counting in a flow cytometer. To do this, the centrifuged cells are resuspended in, for example, 100 microliters of PBS and transferred to the tubes of a test tube strip. Preferably, a single-orientation pipette and two single-orientation racks each having a paper strip are used for this transfer. Additional buffer, e.g., 200-400 microliters of PBS, are added to the tubes to achieve the proper cell concentration for the particular flow cytometer being used. Individual tubes are then broken off from the test tube strip and placed into vessels 84 compatible with the sample port of the flow cytometer, e.g., 12×75 mm test tubes. Finally, the stained cells are analyzed using the flow cytometer to complete the process.

Although specific embodiments of the invention have been described and illustrated, it is to be understood that modifications can be made without departing from the invention's spirit and scope. For example, rack 14 and microtiter plate 16 need not be a separate elements but can be combined as a single unit having orientation means which mate with corresponding orientation means on multichannel pipette 13. Similarly, rather than using the tube-in-a-tube approach for transferring stained cells to the flow cytometer, tubes from a test tube strip can be directly placed onto modified cytometer sample ports or stained cells in microtiter wells may be directly introduced into the flow cytometer via automated equipment.

What is claimed is:

1. Pipetting apparatus comprising:
   (a) manually-manipulable receptacle means comprising an array of receptacles for holding one or more fluids, said means having first and second ends and said array extending between said ends;

(b) manually-manipulable pipette means comprising an array of pipettes for dispensing one or more fluids, said means having first and second ends and said array extending between said ends; and (c) a rack having first and second ends and including first means for manually receiving the receptacle means and second means for manually receiving the pipette means to that the pipettes of the pipette means are in alignment with at least some of the receptacles of the receptacle means when the receptacle means is received by the first means and the pipette means is received by the second means; said pipette means including (i) handle means for manually inverting and removing the pipette means from the rack, and (ii) third means, which engages with the second means when the pipette means is received by the second means, for insuring that the pipette means can only be received by the rack when the pipette means' first and second ends are respectively aligned with the rack's first and second ends.

2. The pipetting apparatus of claim 1 wherein the array of receptacles is composed of a plurality of rows of receptacles, each row extending between the receptacle means' first and second ends, and wherein the rack includes a plurality of second means for manually receiving the pipette means, the third means being engagable with each of the plurality of second means, the pipettes being in alignment with one of the plurality rows of receptacles when the third means is in the engagement with one of the plurality of second means.

3. The pipetting apparatus of claim 2 wherein the receptacle means includes receptacle-orienting means, which engages with the first means when the receptacle means is received by the first means, for insuring that the receptacle means can only be received by the rack when the receptacle means' first and second ends are respectively aligned with the rack's first and second ends.

4. The pipetting apparatus of claim 2 further including means for indicating the engagement of the third means with individual second means of the plurality of second means.

5. The pipetting apparatus of claim 2 further including means for inhibiting multiple engagement of the third means with individual second means of the plurality of second means.

6. The pipetting apparatus of claim 5 wherein the means for inhibiting is resettable.

7. The pipetting apparatus of claim 1 wherein the receptacle means includes receptacle-orienting means, which engages with the first means when the receptacle means is received by the first means, for insuring that the receptacle means can only be received by the rack when the receptacle means' first and second ends are respectively aligned with the rack's first and second ends.

8. A multichannel pipette for manual are with a rack, said rack having first and second ends, said multichannel pipette comprising:
(a) a body which has first and second ends;
(b) an array of pipettes carried by the body;
(c) first means associated with the body for manually engaging the multichannel pipette with the rack and for insuring that the multichannel pipette can only be engaged with the rack when the body's first and second ends are respectively aligned with the rack's first and second ends; and
(d) handle means for manually inserting and removing the multichannel pipette from the rack.

9. The multichannel pipette of claim 8 wherein the first means comprises first and second geometric shapes associated respectively with the first and second ends of the body which engage complementary first and second geometric shapes associated respectively with the first and second ends of the rack.

10. A rack for use with a multichannel pipette, said multichannel pipette having first and second ends and a handle for manual manipulation, said rack comprising:
(a) a body which has first and second ends; and
(b) first means associated with the body for manual engagement with the multichannel pipette and for insuring that the multichannel pipette can only be engaged with the rack when the multichannel pipette's first and second ends are respectively aligned with the body's first and second ends.

11. The rack of claim 10 wherein the first means comprises first and second geometric shapes associated respectively with the first and second ends of the body which engage complementary first and second geometric shapes associated respectively with the first and second ends of the multichannel pipette.

12. The rack of claim 10 wherein the body includes a plurality of said first means.

13. The rack of claim 12 including second means for indicating the engagement of a multichannel pipette with individual first means of the plurality of first means.

14. The rack of claim 12 including means for inhibiting multiple engagements of a multichannel pipette with individual first means of the plurality of first means.

15. The rack of claim 14 wherein the means for inhibiting is resettable.

16. The rack of claim 10 for use with a manually-manipulable array of receptacles, said array having first and second ends, said rack further including receptacle-orienting means associated with the body for manual engagement with the array and for insuring that the array can be engaged with the rack when the array's first and second ends are respectively aligned with the body's first and second ends.

17. The rack of claim 16 wherein the receptacle-orienting means comprises first and second geometric shapes associated respectively with the first and second ends of the body which engage complementary first and second geometric shapes associated respectively with the first and second ends of the array.

18. Pipetting apparatus comprising:
(a) an array of receptacles for holding one or more fluids;
(b) a manually-manipulable, multichannel pipette which has first and second ends and a handle for manual manipulation; and
(c) a rack for holding the array of receptacles and for manually receiving the multichannel pipette, said rack having first and second ends;
said multichannel pipette and said rack each including orientation means which cooperate with each other to insure that the pipette can only be received by the rack when the pipette's first and second ends are respectively aligned with the rack's first and second ends.

* * * * *